United States Patent [19]

Uemura et al.

[11] Patent Number: 4,562,138
[45] Date of Patent: Dec. 31, 1985

[54] NITROGEN-CONTAINING HETEROCYCLIC BLOCKED MERCAPTO DEVELOPMENT INHIBITORS

[75] Inventors: Morito Uemura; Kaoru Onodera, both of Hino, Japan

[73] Assignee: Konishiroku Photo Industry Co., Ltd., Tokyo, Japan

[21] Appl. No.: 642,695

[22] Filed: Aug. 21, 1984

Related U.S. Application Data

[63] Continuation of Ser. No. 450,005, Dec. 15, 1982, abandoned, which is a continuation of Ser. No. 138,931, Apr. 10, 1980, abandoned.

[30] Foreign Application Priority Data

Apr. 17, 1979 [JP]   Japan ................................. 54-46841
Apr. 17, 1979 [JP]   Japan ................................. 54-46842

[51] Int. Cl.$^4$ .......................... G03C 5/54; G03C 1/40; G03C 1/34
[52] U.S. Cl. .................................... 430/219; 430/382; 430/390; 430/445; 430/544; 430/559; 430/611; 430/957; 430/960
[58] Field of Search ............... 430/219, 382, 445, 544, 430/611, 957, 960, 959, 955, 390, 559

[56] References Cited

U.S. PATENT DOCUMENTS

| | | | |
|---|---|---|---|
| 3,260,597 | 7/1966 | Weyerts et al. | 430/219 |
| 3,844,788 | 10/1974 | Burness et al. | 430/955 |
| 4,009,029 | 2/1977 | Hammond et al. | 430/219 |
| 4,246,333 | 1/1981 | Fuseya et al. | 430/219 |
| 4,297,431 | 10/1981 | Sullivan | 430/215 |
| 4,355,101 | 10/1982 | Mehta et al. | 430/219 |

FOREIGN PATENT DOCUMENTS 2427183  12/1974  Fed. Rep. of Germany ...... 430/219

*Primary Examiner*—Richard L. Schilling
*Attorney, Agent, or Firm*—Jordan B. Bierman

[57] ABSTRACT

This invention relates to nitrogen containing heterocyclic compounds represented by the general formula

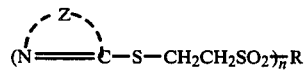

wherein Z is non-metallic atoms necessary to form a tetrazole, a benzotriazole or a benzothiazole, either substituted or unsubstituted, n is either 1 or 2 and R is alkyl or phenyl. The above mentioned compounds can be suitably used in a photographic material as a development inhibitor precursor.

11 Claims, No Drawings

NITROGEN-CONTAINING HETEROCYCLIC BLOCKED MERCAPTO DEVELOPMENT INHIBITORS

This application is a continuation of Ser. No. 450,005, filed Dec. 15, 1982, now abandoned, which is a continuation of Ser. No. 138,931, filed Apr. 10, 1980, now abandoned, which claims priority of Japanese Application No. 46842/1979, also filed on Apr 17, 1979.

This invention relates to a novel nitrogen-containing heterocyclic compound and particularly to a novel nitrogen-containing heterocyclic compound suitable for photographic use. More particularly the present invention relates to a novel nitrogen-containing heterocyclic compound which can suitably be used in a photographic material as a development inhibitor precursor.

A photographic material which consists of a photosensitive element which comprises on a support at least one silver halide emulsion layer associated therewith a dye image forming substance and an image receiving layer, of which photographic material contains a development inhibitor precursor is heretofore known, for example by the disclosure of the U.S. Pat. Nos. 3,265,498, 3,260,597, 3,575,699, 3,649,267 and 4,009,029 and British Pat. No. 1,475,769. Particularly in U.S. Pat. Nos. 3,265,498 and 3,260,597, an art of retarding for certain time the effect of development inhibition by a development inhibitor released from a development inhibitor precursor, is disclosed. By such prior art, however, due to excessive development inhibition owing to insufficient delay of development inhibiting action or, on the contrary owing to excessive delay of the development inhibiting effect, which causes occurrence of color mixture, insufficient maximum density or excessive minimum density (fog), it has been almost impossible to obtain good dye images. Further, in U.S. Pat. Nos. 3,575,699 and 3,649,267 art for reducing fog forming for the broad range of processing temperature by the use of a development inhibitor precursor which can release the development inhibitor more rapidly as the temperature rises, and thus to broaden processing temperature latitude is disclosed.

However, by the use of such heretofore known development inhibitor releasing precursors, insufficient temperature dependency of development inhibitor releasing rate from such development inhibitor releasing precursor has been still observed. Namely, a development inhibitor releasing precursor that has a suitable development inhibitor releasing rate at high temperature tends to release a development inhibitor too fast at low temperature with the result that necessary development is excessively restrained and, on the contrary, a development inhibitor releasing precursor that has a suitable development inhibitor releasing rate at low temperature tends to release a development inhibitor too slow at high temperature, resulting in excessive progress of development. Consequently, it has been impossible by means of such prior art to control development inhibition properly for extended temperature range (especially at high temperature) and thus to obtain good dye images. Therefore, it is an primary object of this invention to solve this problem which has remained unsolved even by such prior art and more particularly to provide a novel nitrogen-containing heterocyclic compound which can suitably be used as a development inhibitor releasing precursor for color photography, and especially for color diffusion transfer photography.

SUMMARY OF THE INVENTION

After our intensive study for the accomplishment of the above-mentioned object, we have hereby discovered a development inhibitor releasing precursor which has desired development inhibitor releasing rate with sufficient temperature dependency. Namely, we have discovered that the above-mentioned object can be accomplished by the use of a compound represented by the following general formula in a photographic materials which comprises on a support at least one photosensitive silver halide emulsion layer and a dye image forming substance:

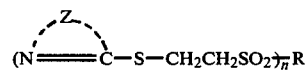

wherein Z represent non-metallic atoms necessary for forming a 5- or 6-membered heterocyclic ring, n represents an integer of 1 or 2 and R represents an alkyl, phenyl, alkylene or phenylene group provided that when n is 1, R represents alkyl group or phenyl group and alkylene or phenylene group when n is 2.

DETAILED DESCRIPTION OF THE INVENTION

In the above general formula as a 5- or 6-membered heterocyclic ring either a monocyclic ring or a fused ring with or without a substituent can be mentioned. As typical examples thereof tetrazole rings such as tetrazole ring and phenyltetrazole ring; triazole rings such as benzotriazole ring and 1,2,4-triazole ring; diazole rings such as benzoimidazole ring and imidazole ring; pyrimidine rings such as pyrimidine ring and monoazole rings such as benzothiazole and benzoxazole can be mentioned. Preferably, the heterocyclic ring having at least two hetero atoms like tetrazole rings, benzotriazole ring and benzothiazole rings can be used and tetrazole ring especially phenyl-substituted tetrazole ring can be mentioned as especially preferable heterocyclic ring.

n is preferably 1. Among alkyl or alkylene groups for R, alkyl or alkylene group having 1 to 25 carbon atoms is preferable and alkyl or alkylene group having 1 to 3 carbon atoms (such as ethyl group or 2-methoxy ethyl group) is especially preferable. Phenyl or phenylene group represented by R may be substituted by, for example, nitro group, cyano group, alkoxyl group having 1 to 25 carbon atoms, alkyl group having 1 to 25 carbon atoms, sulfo group, amido group such as alkane amido having 1 to 25 carbon atoms or halogen atom such as chlorine atom as a preferable example. Among groups for R, alkyl group or phenyl group having no substituent or been substituted by electron donative group (such as alkoxyl group) is preferable and phenyl group having no substituent is more preferable.

Among the development inhibitor releasing precursors of the present invention those having, as the heterocyclic ring including Z, 1,2,3,4-tetrazole ring or 1-phenyl-1,2,3,4-tetrazole ring and as R phenyl group having no substituent is preferable and the most preferable is exemplified compound 1 described hereinafter.

It is assumed that an object of this invention is attained because the compounds of this invention can release a development inhibitor

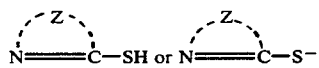

group timely at proper speed at broad range of temperature in alkali medium for processing a photographic material and the said favorable releasing of the development inhibitor is considered to be mainly caused in particular by R—SO$_2$— group in —CH$_2$CH$_2$SO$_2$)$_n$—R, which is protection group portion of said development inhibitor releasing precursor.

Although compounds which have similar chemical structures to the development inhibitor releasing precursor of the present invention and which have, as a protection group portion containing CH$_3$CO—group or CH$_3$COCH$_2$CH$_2$—group is known, it has been revealed by the present inventor that although both R—SO$_2$—group and R—CO—group are the groups that belong to a category of acyl group, that the use of a compound of the present invention having R—SO$_2$—group in its structure can give better dye image and especially when the photographic material is to be processed at high temperature, a good dye image with a low minimum density and a high maximum density can be obtained.

Typical examples of the compounds of the present invention are shown as follows.

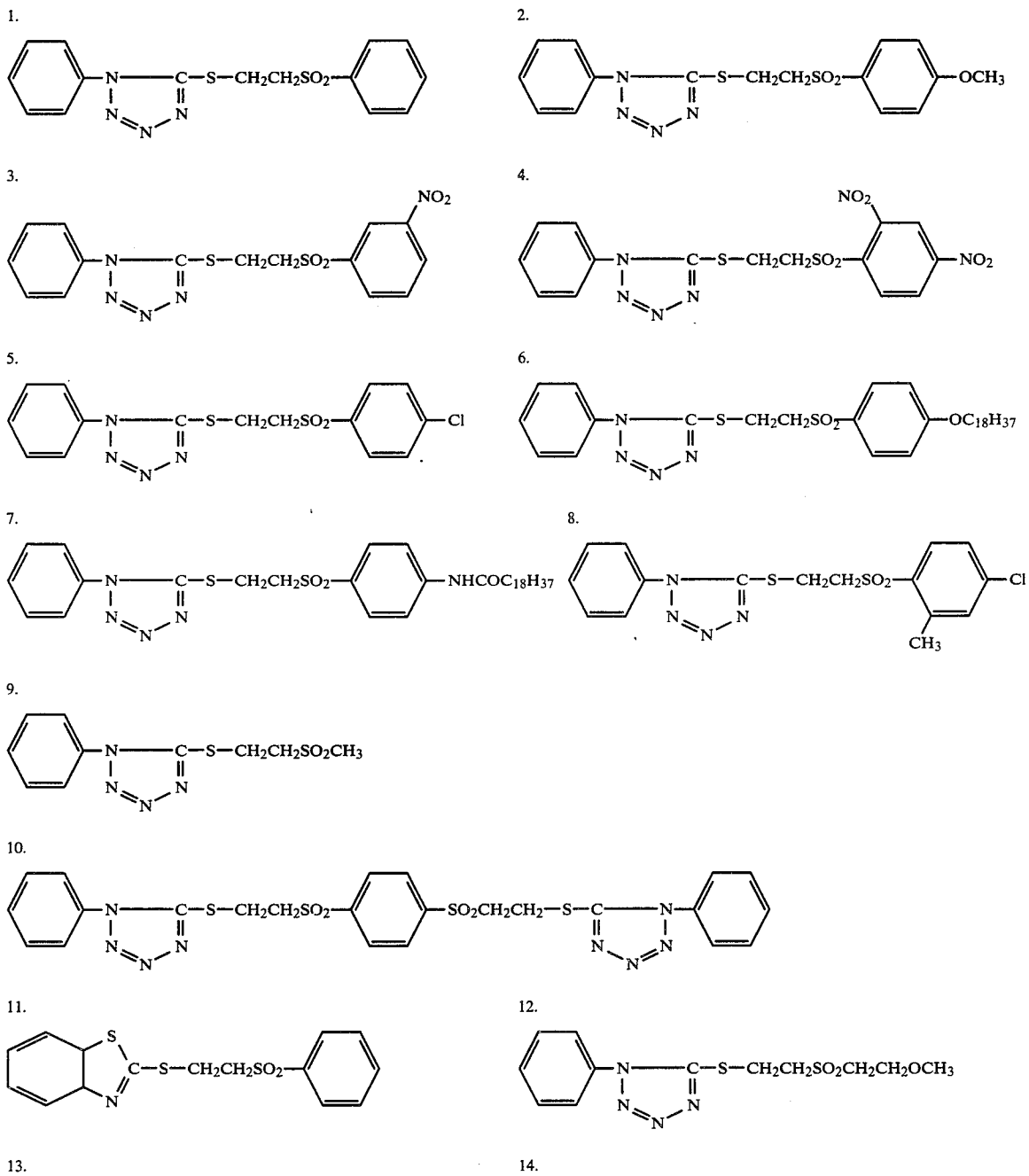

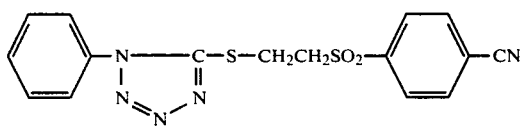

The nitrogen-containing heterocyclic compound of the present invention can be synthesized by heating alkali metal salt of a compound represented by the formula

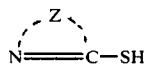

and β-halogenoethylsulfon compound (X—CH$_2$CH$_2$SO$_2$)$_n$—R (where, X represents halogen atom and each of Z, n and R has the same meaning as the one mentioned above) in a suitable solvent such as acetone, methyl alcohol and the like.

Typical synthesis examples are given below.

SYNTHESIS EXAMPLE 1 (SYNTHESIS OF EXEMPLIFIED COMPOUND 1)

2.0 g of phenyl-β-chloroethylsulfon and 2.0 g of 1-phenyl-5-mercapto-1,2,3,4-tetrazole sodium salt were added to 50 ml of acetone and after one hour of reflux, the reaction mixture was condensed. After the extraction with 50 ml of ethyl acetate, the extract was washed with water and further was washed with aqueous sodium bicarbonate solution. After drying with sodium sulfate anhydride, the extract was condensed and then the residue was recrystallized in 30 ml of methyl alcohol. The yield amount was 2.5 g and the melting point of the resulted compound was 110°–111° C. By means of mass spectrum analysis, a parent peak of 346 was detected:

The results of the elementary analysis are as follows:

| % | C | H | N |
|---|---|---|---|
| Theoretical value | 52.01 | 4.07 | 16.17 |
| Measured value | 52.13 | 4.11 | 16.05 |

It was determined from the results of the elementary analysis and the mass spectrum analysis that the compound synthesized was exemplified compound 1.

SYNTHESIS EXAMPLE 2 (SYNTHESIS OF EXEMPLIFIED COMPOUND 2)

Synthesis was carried out in the same manner as synthesis example 1 except that 3 g of p-methoxyphenyl-β-chloroethylsulfon was used instead of 2 g of phenyl-β-chloroethylsulfon in synthesis example 1. The yield amount was 2.0 g and the melting point of the resulted was 87°–88° C. As a result of mass spectrum analysis, a parent peak of 376 was detected.

The results of the elementary analysis are as follows:

| % | C | H | N |
|---|---|---|---|
| Theoretical value | 51.05 | 4.28 | 14.88 |
| Measured value | 51.02 | 4.33 | 14.81 |

From the results of the elementary analysis and the mass spectrum analysis, it was determined that the compound was exemplified compound 2.

SYNTHESIS EXAMPLE 3 (SYNTHESIS OF COMPOUND 3)

Synthesis was carried out in the same manner as synthesis example 1 except that 3.3 g of m-nitrophenyl-β-chloroethylsulfon was used instead of 2.0 g of phenyl-β-chloroethylsulfon in synthesis example 1 and 50 ml of acetonitrile was used for recrystallization instead of 30 ml of methyl alcohol. The yield amount was 3.2 g and the melting point was 165°–166° C. By means of mass spectrum analysis, a parent peak of 391 of was detected.

The results of the elementary analysis are as follows:

| % | C | H | N |
|---|---|---|---|
| Theoretical value | 46.03 | 3.35 | 17.89 |
| Measured value | 45.98 | 3.44 | 18.07 |

From the results of the elementary analysis and the mass spectrum analysis, it was determined that the compound was exemplified compound 3.

SYNTHESIS EXAMPLE 4 (SYNTHESIS OF COMPOUND 9)

Synthesis was carried out in the same manner as synthesis example 1 except that 1.8 g of methyl-β-chloroethylsulfon was used instead of 2.0 g of phenyl-β-chloroethylsulfon in synthesis example 1. The yield amount was 1.5 g and the melting point of the resulted compound was 138°–139.5° C. As a result of mass spectrum analysis, a parent peak of 284 was detected.

The results of the elementary analysis are shown as follows.

| % | C | H | N |
|---|---|---|---|
| Theoretical value | 42.24 | 4.25 | 19.70 |
| Measured value | 42.17 | 4.30 | 19.58 |

It was determined from the results of the elementary analysis and the mass spectrum analysis that the compound was exemplified compound 9.

According to one of preferable embodiments of the invention the nitrogen-containing heterocyclic compound of the invention is used for a photographic material which comprises on a support at least one photosensitive silver halide emulsion layer having been associated therewith a dye image forming substance.

According to another preferable embodiment of the invention the nitrogen-containing heterocyclic compound is used for a color diffusion transfer photographic material comprising on a support at least one photosensitive silver halide emulsion layer having been associated therewith a dye image forming substance and a dye image-receiving layer.

The nitrogen-containing heterocyclic compound of the present invention represented by the general formula described above can suitably be used as a development inhibitor releasing precursor for photography and is preferably contained in a layer into which the process composition can penetrate during development process (hereinafter referred to as processing composition penetrating layer).

As the processing composition penetrating layer, for example, a photosensitive silver halide emulsion layer and a protective layer can be mentioned. For the photographic material mentioned above in which a photosensitive silver halide emulsion layer has associated therewith a dye image forming substance, an interlayer can be mentioned as a processing composition penetrating layer in addition to the photosensitive silver halide emulsion layer and a protective layer.

In color diffusion transfer photographic material there can be mentioned as the processing composition penetrating layers, neutralizing layer, timing layer, opaque layer, light-reflection layer, protective layer, interlayer, stripping layer, physical development nucleus layer, previously fogged silver halide emulsion layer and dye image forming substance layer in addition to the said photosensitive silver halide emulsion layer and image receiving layer.

Among the said various process composition penetrating layers, the preferable layers are interlayer, protective layer, dye image forming substance layer, photosensitive silver halide emulsion layer, timing layer, light-reflection layer, opaque layer, physical development nucleus layer and previously fogged silver halide emulsion layer and more preferable are interlayer, protective layer, dye image forming substance layer, photosensitive silver halide emulsion layer and timing layer and the most preferable is timing layer.

In case of incorporation of the compound of the invention into a timing layer of such a color diffusion transfer photographic material having two timing layers as disclosed in the U.S. Pat. No. 4,061,496, which color diffusion transfer photographic material consists of, on a support, as essential layers, a neutralizing layer, timing layer comprising polymer latex and having an activation energy of penetration of the layer by aqueous alkaline solution of less than 18 Kcal/mole and timing layer comprising a polymer latex and having an activation energy of penetration of the layer by an aqueous alkaline solution of more than 18 Kcal/mole in this order, the preferable is the timing layer having an activation energy of penetration of the layer by alkaline solution of less than 18 Kcal/mole.

The amount of the present compound to be added can vary depending upon the kind the compound or layer to be added, adding method and the like, but generally speaking, the amount is from 0.001 mole to 1.0 mole per 1 mole of photosensitive silver halide used and the preferable range is from 0.005 mole to 0.1 mole and, especially, when the development inhibitor formed from the development inhibitor releasing precursor in the alkaline medium is 1-phenyl-5-mercapto-1,2,3,4-tetrazole, the range of 0.02 mole to 0.1 mole is preferable.

The development inhibiting releasing precursor of the invention can be added into a processing composition penetrating layer by various methods heretofore known, and it is especially preferable to dissolve the said precursor in a water miscible organic solvent such as aceton, methanol and ethanol, and to add it into a coating composition for the processing composition penetrating layer.

In the photographic material according to this invention, the photosensitive silver halide emulsion layer may be associated with various dye image forming substances. For example, as a dye image forming substance various type of color couplers, such disclosed in U.S. Pat. Nos. 3,046,129 and 3,620,747 as typical examples can be used to form a dye image when a color developing agent is used in a processing composition.

Substantially non-diffusible color image forming substances in an alkaline medium for color diffusion transfer photography can also be mentioned as typical image forming substances, which include so-called dye releasing redox compounds (DRR compounds), as disclosed in U.S. Pat. Nos. 4,076,529, 4,055,428 and 3,443,939; French Pat. No. 2,284,140 and Japanese Patent Publications for open to public inspection 53-46730/1978, 53-50736/1978, 51-113624/1971 and 53-3819/1978; non-diffusible image forming substances which can release diffusible dye in alkaline medium, as disclosed in Japanese Patent publications open to public inspection 49-111628/1974 and 51-63618/1976; and so-called BEND compounds as disclosed in U.S. Pat. Nos. 4,139,379 and 4,139,389; diffusible dye releasing couplers, as disclosed in U.S. Pat. No. 3,227,550. Substantially, diffusible dye image forming substance in the alkaline medium can also be mentioned and it includes, for example, so-called dye developers as disclosed in U.S. Pat. Nos. 3,983,606, 3,880,658, 3,854,945 and 3,563,739.

In this invention, the particularly useful dye image forming substances are dye releasing redox compound, and dye developer. Further, the more useful dye image forming substance is dye releasing redox compound.

As for photosensitive silver halide emulsion any of those which are heretofore known can be used and it may be either negative type or positive type. When positive type is used so-called internal image direct positive silver halide emulsion is preferably used.

As a photographic material for use of color diffusion transfer, any of those which are heretofore known can be used. As the preferable materials for this use, the following two kinds can be mentioned as typical examples. The first one of this type comprises on a support at least one photosensitive silver halide emulsion layer which is combined with a dye image forming substance and an image receiving layer coated on a different support; and the second type comprises a processing sheet and a support having thereon at least one photo-sensitive silver halide emulsion layer having been associated with a dye image forming substance, and image receiving layer, both on the same side of the support. In the first type of photographic material the two supports are so arranged that the photosensitive silver halide emulsion layer and the image receiving layer may locate in between the two supports when processed by processing composition, and in the second type, the support and the processing sheet may be so arranged that the photosensitive silver halide emulsion layer and image receiving layer and may locate in between the said support and processing sheet.

A neutralizing layer may be used for in a color diffusion transfer photographic material of this invention for preventing image from discoloration and contamination which may be caused by high pH, by increasing dye image stability and by substantially stopping furhter diffusion of diffusible dye by lowering pH, after substantially forming a color dye image on an image receiving layer by means of processing by alkaline processing composition.

The timing layer, which may be used for this invention, retards pH decrease until after desirable development and image transfer complete.

The neutralizing layer and timing layer may be coated on a support on which a photosensitive silver halide emulsion layer and/or image receiving layer are coated, and it is preferable that neutralizing layer, timing layer, silver halide emulsion layer and/or image receiving layer are coated in this order from said support side. Also, the neutralizing layer and/or timing layer may be coated on a processing sheet and in this case it is preferable that the neutralizing layer and the timing layer are coated in this order on a support of processing sheet. In case that the processing sheet having this neutralizing layer and timing layer is used in the said second type of photographic material for use of color diffusion transfer, each of the two supports may be so positioned as to put photosensitive silver halide emulsion layer, image receiving layer, timing layer and neutralizing layer in between the said supports when processed by processing composition.

The support used for the photographic material of the present invention, may be of either transparent, opaque or semi-transparent, according to purposes.

In case that the photographic material is used as color print paper, a background of formed image is necessary. As a background it is common to form light-reflection layer having high whiteness on the opposite side of an observing direction with respect to an image receiving layer. When the silver halide emulsion is developed in a light room after exposure, it is preferable to have an opaque layer for the purpose of protecting the silver halide emulsion from light.

In this case, the support may function as a light reflection layer and said opaque layer or a light reflection layer and/or opaque layer may be formed either in advance or during image formation process.

In case that a multi-color dye image is to be formed by making use of a color diffusion transfer photographic material of the invention, it is preferable to use more than two combination units of photosensitive silver halide emulsion layer and dye image forming substance, and in case that the color sensitivity of the above combination units are different from each other, it is advantageous to have an interlayer in between the each combination unit. The said interlayer prevents from undesirable interaction which may occur in between combination units and at the same time controls diffusion of diffusible dye or its precursor and alkaline processing composition. A protective layer may be put when it is necessary in an appropriate position.

An image forming substance may preferably be incorporated into a color diffusion transfer photographic material so that it may not reduce the sensitivity of photosensitive silver halide emulsion used together with the said dye image forming substance. That is, when spectral absorption of dye image forming substance falls substantially in the same spectral regeon as that of photosensitive silver halide emulsion layer, it is preferable that the said dye image forming substance is to be incorporated in a layer which is positioned on the opposite side of exposure side with respect to said photosensitive silver halide emulsion layer. When, on the other hand, the dye image forming substance itself does not presume color at the time of exposure like a conventional type colorless dye forming coupler, leuco type color dye or shift type color dye, it may be incorporated either in a photosensitive silver halide emulsion layer, or even in a layer on the exposure side with respect to said silver halide emulsion layer.

In a photographic material of the present invention, various kinds of photosensitive silver halide emulsion may be used in combination with a dye image forming substance depending on the purpose.

Typical examples of silver halide emulsion and image forming processes, which may be employed in the present invention include those disclosed in U.S. Pat. Nos. 3,227,552, 2,592,250, 2,005,837, 3,367,778, 3,761,276, British Pat. No. 1,011,062, the Japanese patent publication 41-17,184/1966, Japanese Patent Publication open to public inspection 50-8,524/1975, British Pat. No. 904,364, Japanese Patent Publication open to public inspection 47-325/1972, Japanese Patent Publication 43-21,778/1968, U.S. Pat. Nos. 3,227,554 and 3,632,345, etc.

As the material used for above-mentioned neutralizing layer, timing layer, light reflection layer, opaque layer, interlayer or protective layer, various kinds of materials heretofore known can be used. In a color diffusion transfer photographic material, a stripping layer may optionally be formed.

In this invention, the particularly preferable color diffusion transfer photographic material may have, at the time of image forming process, image receiving layer, light reflection layer, opaque layer, dye image forming substance layer, photosensitive silver halide emulsion layer, timing layer and neutralizing layer between two transparent supports, and at the time of image formation, processing composition may preferably be spread in between said silver halide emulsion layer and said timing layer. Another preferable type comprises as essential layers dye image forming substance containing layer, silver halide emulsion layer, image receiving layer, timing layer and neutralizing layer in this order from the side of an opaque support in between opaque support and transparent support, and alkaline processing composition containing opaque agent may be spread in between said silver halide emulsion layer and said image receiving layer. A particularly useful color diffusion transfer photographic material for obtaining multi-color dye image may comprise as essential layers image receiving layer, light reflection layer, opaque layer, cyan dye image forming substance containing layer, red-sensitive silver halide emulsion layer, interlayer, magenta dye image forming substance containing layer, green-sensitive silver halide emulsion layer, interlayer, yellow dye image forming substance containing layer, blue-sensitive silver halide emulsion layer, protective layer, timing layer and neutralizing layer in this order between two transparent supports, and at the time of process, the alkaline processing composition containing an opaque agent may be spread between said protective layer and said timing layer. Another particularly preferable type may comprise as essential layers cyan dye image forming substance containing layer, red-sensitive silver halide emulsion layer, interlayer, magenta dye image forming substance containing layer, green-sensitive silver halide emulsion layer, interlayer, yellow dye image forming substance containing layer, blue-sensitive silver halide emulsion layer, protective layer, image receiving layer, timing layer and neutralizing layer in this order between an opaque support and a transparent support from the side of opaque support, and the alkaline processing composition containing opaque agent may be spread between said protective layer and said image receiving layer.

The processing composition to process a color diffusion transfer photographic material of the present invention is generally made of an alkaline composition and it contains an alkali agent and has pH value of more than about 10 at room temperature. By the use of this alkaline composition, alkaline condition in which a development inhibitor can be released from the development inhibitor releasing precursor. It is preferable that the processing composition contains viscous agent so that it may have viscosity of about 100-300,000 centi poise. Thus it is possible to make the uniform distribution of the process composition in processing and further during precessing the non-fluid film is formed resulting in the effect to prevent the undesirable change of an image after the substantial formation of dye image. When a dye image forming substance having no silver halide developing function is used, a developing agent for silver halide is used. Further, even when dye image forming substance itself has such developing function, it is preferable to use the developing agent for silver halide as an auxiliary means. Such developing agent for silver halide is ordinarily incorporated in processing composition and/or processing composition penetrating layer of the photographic material. In addition, the processing composition may, according to silver halide emulsion used, contain silver halide solvent and other various kinds of known and commonly used additives. As a means to apply processing composition to color diffusion transfer photographic material of the present invention, various ways ever known may suitably be employed and the use of a ruptuable pod may preferably be applied.

The present invention is described in detail with reference to examples below.

EXAMPLE 1

An integral three color photographic element 1 (control) for color diffusion transfer process was prepared by coating, on a transparent polyethyleneterephthalate film support of 150 μm in thickness, following layers. In the examples hereinbelow the figure in parentheses, ( ), hereinbelow with respect to respective layers with a dimension of mg/100 cm$^2$ represent the coating amount, unless so specified otherwise. For further reference, the chemical structural formulae of fluorescent brightener and dye-image forming substances A to I used in the examples are shown at the end of the example 9.

(1) An image-receiving layer comprising a terpolymer of styrene, N,N-dimethyl-N-benzyl-N-p-(methacryloyl aminophenyl)methylammonium chloride and divinylbenzene (molar ratio: 48/48/4) (27 mg/100 cm$^2$), fluorescent brightener (0.4 mg/100 cm$^2$) and gelatin (27 mg/100 cm$^2$).

(2) A light reflecting layer comprising titanium dioxide (230 mg/100 cm$^2$) and gelatin (22 mg/100 cm$^2$).

(3) An opaque layer comprising carbon black (25 mg/100 cm$^2$) and gelatin (17 mg/100 cm$^2$).

(4) A cyan DRR containing layer comprising cyan DRR compound A (6 mg/100 cm$^2$), 2-acetyl-5-sec-octadecylhydroquinone (0.3 mg/100 cm$^2$), N,N-diethyllaurylamido (6 mg/100 cm$^2$) and gelatin (14.4 mg/100 cm$^2$).

(5) A photosensitive silver halide emulsion layer comprising red-sensitive internal image direct positive silver bromide emulsion (11 mg/100 cm$^2$ based on silver), 2-sec-octadecylhydroquinone-5-sulfonic acid potassium salt (1.3 mg/100 cm$^2$), 1-acetyl-2-{4-[5-amino-2-(2,4-di-tert-amylphenoxy)benzamido]phenyl}-hydrazine (100 mg/mole of silver), 1-[4-(2-formylhydrazino)phenyl]-3-phenylthiourea (0.5 mg/mole silver), and gelatin (17.5 mg/100 cm$^2$).

(6) An interlayer comprising 2-acetyl-5-sec-octadecylhydroquinone (4.5 mg/100 cm$^2$), dibutylphthalate (2.25 mg/100 cm$^2$) and gelatin (10.0 mg/100 cm$^2$).

(7) A magenta DRR compound containing layer which comprises magenta DRR compound B (8.0 mg/100 cm$^2$), 2-acetyl-5-sec-octadecylhydroquinone (0.4 mg/100 cm$^2$), N,N-diethyllaurylamido (0.8 mg/100 cm$^2$) and gelatin (16.0 mg/100 cm$^2$)

(8) A photosensitive silver halide emulsion layer comprising green sensitive internal image direct positive sivler bromide emulsion (11 mg/100 cm$^2$ based on silver), 2-sec-octadecylhydroquinone-5-sulfonic acid potassium salt (1.3 mg/100 cm$^2$), 1-acetyl-2-{4-[5-amino-2-(2,4-di-tert-amylphenoxy)benzamido]phenyl}-hydrazine (300 mg/mole silver 100 cm$^2$), 1-[4-(2-formylhydrazino)phenyl]-3-phenylthiourea (1 mg/mole of silver) and gelatin (17.5 mg/100 cm$^2$).

(9) An interlayer comprising 2-acetyl-5-sec-octadecylhydroquinone (4.5 mg/100 cm$^2$), dibutylphthalate (2.25 mg/100 cm$^2$) and gelatin (10.0 mg/100 cm$^2$).

(10) A yellow DRR compound containing layer which comprises yellow DRR compound C (10.0 mg/100 cm$^2$), 2-acetyl-5-sec-octadecylhydroquinone (0.4 mg/100 cm$^2$), tricresylphosphate (10.0 mg/100 cm$^2$) and gelatin (20.0 mg/100 cm$^2$).

(11) A photosensitive silver halide emulsion layer comprising blue-sensitive internal image direct positive silver bromide emulsion (14 mg/100 cm$^2$ based on silver), 2-sec-octadecylhydroquinone-5-sulfonic acid potassium salt (1.6 mg/100 cm$^2$), 1-acetyl-2-{4-[5-amino-2-(2,4-di-tert-amylphenoxy)benzamido]phenyl}-hydrazine (500 mg/mole silver), 1-[4-(2-formylhydrazino)-phenyl]-3-phenylthiourea (3 mg/mole silver) and gelatin (23 mg/100 cm$^2$).

(12) A protective layer comprising 2-acetyl-5-sec-octadecylhydroquinone (4.5 mg/100 cm$^2$), dibutylphthalate (2.25 mg/100 cm$^2$), 1,3,5-tri-acryloyl-hexahydro-s-triazine (2 mg/100 cm$^2$), N,N'-bis(1-aziridinecarbonyl)-hexamethylenediamine (2 mg/100 cm$^2$) and gelatin (20 mg/100 cm$^2$).

Then photographic elements 2 to 4 were prepared in the following manner.

PHOTOGRAPHIC ELEMENT 2 (COMPARISON)

This photographic element was prepared in the same manner as photographic element 1, except that $2 \times 10^{-6}$ mol/100 cm$^2$ (0.4 mg/100 cm$^2$) of 1-phenyl-5-mercaptotetrazole was incorporated into each of the above mentioned layers (6), (9) and (12).

PHOTOGRAPHIC ELEMENT 3 (COMPARISON)

This photographic element was prepared in the same manner as photographic element 2, except that 1-phenyl-5-mercaptotetrazole in the element 2 was replaced by 5-(2-acetyl-ethylthio)-1-phenyltetrazole.

PHOTOGRAPHIC ELEMENT 4 (THIS INVENTION)

This photographic element was prepared in the same manner as photographic element 2, except that 1-phenyl-5-mercaptotetrazole in the element 2 was replaced by 5-(2-phenylsulfonyl-ethylthio)-1-phenyltetrazole.

Each of four kinds of photographic element thus prepared was exposed to a given amount of light and then was superimposed on a processing sheets described below thereby to form four color diffusion photographic materials. And thereafter four film units were prepared by interpositioning a rupturable pod which contains the following alkaline processing composition between the photographic element and the processing sheet. The pod was ruptured by squeezing the film unit through a pair of juxtaposed pressure rollers and the processing composition was spread out between above mentioned protective layer and the gelatin layer of the following processing sheet so that the thickness of the processing composition layer became 80 μm.

A PROCESSING SHEET

This processing sheet consists of gelatin (45 mg/100 cm$^2$) and mucochloric acid (0.4 mg/100 cm$^2$) coated on a transparent polyethylene terephthalate film support of 100 μm thickness.

| Processing composition: | |
|---|---|
| Potassium hydroxide | 67 g |
| Sodium hydroxide | 3.4 g |
| 4-hydroxymethyl-4-methyl-1-phenyl-3-pyrazolidone | 12.6 g |
| Sodium sulfite | 2.0 g |
| 5-methylbenzotriazole | 3.4 g |
| 2-tert-butylhydroquinone | 0.3 g |
| 2-methylhydroquinone | 0.1 g |
| Carboxymethylcellulose.sodium salt | 60.0 g |
| Carbon black | 171 g |
| Distilled water to make | 1,000 ml |

Each of thus processed film units were left alone for ten minutes after processing. Subsequently, the photographic element was removed from the pod and the processing sheet and then immediately soaked into 5% acetic acid aqueous solution. After washing and drying, the obtained reflection density of dye image (maximum density: Dmax and minimum density: Dmin) were measured at varied temperatures of 15° C., 23° C. and 38° C.

TABLE 1

| Photographic element | 15° C. | | 23° C. | | 38° C. | |
|---|---|---|---|---|---|---|
| | Dmax | Dmin | Dmax | Dmin | Dmax | Dmin |
| 1 (Control) | | | | | | |
| Blue | 1.15 | 0.20 | 1.35 | 0.22 | 1.72 | 0.50 |
| Green | 1.21 | 0.19 | 1.62 | 0.20 | 1.92 | 0.60 |
| Red | 1.45 | 0.22 | 1.58 | 0.24 | 1.95 | 0.58 |
| 2 (Comparison) | | | | | | |
| Blue | 0.92 | 0.20 | 1.07 | 0.20 | 1.33 | 0.21 |
| Green | 0.90 | 0.19 | 1.05 | 0.18 | 1.28 | 0.20 |
| Red | 0.98 | 0.18 | 1.07 | 0.19 | 1.25 | 0.20 |
| 3 (Comparison) | | | | | | |
| Blue | 1.10 | 0.19 | 1.20 | 0.20 | 1.48 | 0.21 |
| Green | 1.06 | 0.20 | 1.30 | 0.19 | 1.55 | 0.24 |
| Red | 1.12 | 0.21 | 1.33 | 0.21 | 1.65 | 0.25 |
| 4 (This Invention) | | | | | | |
| Blue | 1.20 | 0.19 | 1.38 | 0.21 | 1.75 | 0.24 |
| Green | 1.22 | 0.20 | 1.65 | 0.19 | 1.93 | 0.31 |
| Red | 1.44 | 0.22 | 1.60 | 0.22 | 1.92 | 0.30 |

From Table 1, it is understood that the photographic element according to this invention (photographic element 4), when compared with other photographic elements shows sufficiently high maximum density (Dmax) with low minimum density (Dmin) even in case of high temperature processing.

EXAMPLE 2

The similar material to photographic element 4 of example 1 was prepared except that the photographic element was incorporated with 0.4 mg/100 cm$^2$ of 5-(2-phenylsulfonylethylthio)-1-phenyltetrazole in each DRR compound containing layers (4), (7) and (10).

The processing and evaluation were made in the similar manner to that in example 1. The similar results to that from the example 1 were obtained.

EXAMPLE 3

The similar material to photographic element 4 of example 1 was prepared except that 0.2 ml/100 cm$^2$ of 5-(2-phenylsulfonyl-ethylthio)-1-phenyltetrazole was incorporated in each of the photosensitive silver halide emulsion layers (5), (8) and (11).

The processing and evaluation were made in the manner mentioned in the example 1. The similar results to that from the example 1 were obtained.

EXAMPLE 4

An integral three color diffusion transfer photographic material was prepared by coating the following layers successively in this order on a transparent polyethyleneterephthalate film support of 150 μm in thickness.

(1) An image-receiving layer comprising a terpolymer of styrene, N,N-dimethyl-N-benzyl-N-p-(methacryloylaminophenyl)methylammoniumchloride and divinylbenzene, (48/48/4 by molar ratio) (26 mg/100 cm$^2$), fluorescent brightener (0.4 mg/100 cm$^2$) and gelatin (27 mg/100 cm$^2$).

(2) A light reflecting layer comprising titanium dioxide (200 mg/100 cm$^2$) and gelatin (27 mg/100 cm$^2$).

(3) A black opaque layer comprising carbon black (17 mg/100 cm$^2$) and gelatin (11 mg/100 cm$^2$).

(4) A cyan DRR compounds containing layer comprising cyan DRR compound D (6 mg/100 cm$^2$), 2-acetyl-5-sec-octadecylhydroquinone (0.3 mg/100 cm$^2$), tricresylphosphate (6 mg/100 cm$^2$) and gelatin (14.4 mg/100 cm$^2$).

(5) A photosensitive silver halide emulsion layer comprising red-sensitive internal image direct positive silver bromide emulsion (16 mg/100 cm$^2$ based on silver), 2-sec-octadecylhydroquinone-5-sulfonic acid potassium salt (1.8 mg/100 cm$^2$), 1-[4-(2-formylhydrazino)-phenyl]-3-phenylthiourea (0.6 mg per mol of silver) and gelatin (17.5 mg/100 cm$^2$).

(6) An interlayer comprising 2-acetyl-5-sec-octadecylhydroquinone (4.5 mg/100 cm$^2$), dibutylphthalate (2.25 mg/100 cm$^2$) and gelatin (10.0 mg/100 cm$^2$).

(7) A magenta DRR compound containing layer comprising magenta DRR compound B (8.0 mg/100 cm$^2$), 2-acetyl-5-sec-octadecylhydroquinone (0.3 mg/100 cm$^2$), tricresylphosphate (8.0 mg/100 cm$^2$) and gelatin (16.0 mg/100 cm$^2$).

(8) A photosensitive sivler halide emulsion layer comprising green-sensitive internal image direct positive silver bromide emulsion (16 mg/100 cm$^2$ based on silver), 2-sec-octadecylhydroquinone-5-potassiumsulfonate (1.8 mg/100 cm²), 1-[4-(2-formylhydrazino)phenyl]-3-phenylthiocarbamide (0.5 mg/mole silver) and gelatin (17.5 mg/100 cm²).

(9) An interlayer comprising 2-acetyl-5-sec-octadecylhydroquinone (4.5 mg/100 cm²), dibutylphthalate (2.25 mg/100 cm²) gelatin (10.0 mg/100 cm²).

(10) A yellow DRR compound containing layer, comprising yellow DRR compound C (10.0 mg/100 cm²), 2-acetyl-5-sec-octadecylhydroquinone (0.4 mg/100 cm²), tricresylphosphate (10.0 mg/100 cm²) and gelatin (20.0 mg/100 cm²).

(11) A photosensitive silver halide emulsion layer comprising blue-sensitive internal image direct positive silver bromide emulsion (18 mg/100 cm² based on silver), 2-sec-octadecylhydroquinone-5-sulfonic acid potassium salt (2.1 mg/100 cm²), 1-[4-(2-formylhydrazino)phenyl]-3-phenylthiourea (3 mg/mole silver) and gelatin (23 mg/100 cm²).

(12) A protective layer comprising 2-acetyl-5-sec-octadecylhydroquinone (4.5 mg/100 cm²), dibutylphthalate (2.25 mg/100 cm²), tetrakis-(vinylsulfonylmethyl)methane (4 mg/100 cm²) and gelatin (20 mg/100 cm²).

Next, the processing sheet A was prepared by coating the following layers in this order on a transparent polyethylene terephthalate film support of 100 μm in thickness.

(a) A neutralizing layer comprising copolymer of acrylic acid and butyl acrylate (70/30 at weight ratio) (200 mg/100 cm²).

(b) A timing layer comprising diacetylcellulose (55 mol% acetylated) (57 mg/100 cm²) and copolymer of styrene and maleic anhydride (1:1) (4.5 mg/100 cm²).

(c) A timing layer comprising terpolymer of vinylidene chloride, acrylonitrile and acrylic acid (79/15/6 by weight ratio).

THE PROCESSING SHEET B

This has the same structure as processing sheet A, except that 3.4 mg/100 cm² of 5-(2-phenylsulfonyl-ethylthio)-1-phenyltetrazole (1×10⁻⁵ mol/100 cm²) was added into timing layer (b) of the processing sheet A.

The photographic elements thus prepared were exposed to a given amount of light through a silver wedge and then superimposed on the above processing sheet, thereby to form photographic materials, and further, the film units were prepared by interpositioning a rupturable pod containing alkaline processing composition given below. By passing these film units between a pair of juxtaposed pressure rollers, the pod was ruptured thereupon, and then the content of the pod was spread out between the protective layer (12) of the photographic element and the timing layer (c) of the processing sheet. Leaving it alone at a certain given temperature for two hours after processing, a reflection density of transferred dye image was measured at temperatures of 15° C., 23° C. and 38° C. Processing composition:

| | |
|---|---|
| Potassium hydroxide | 67 g |
| Sodium hydroxide | 3.4 g |
| 4-hydroxymethyl-4-methyl-1-phenyl-3-pyrazolidone | 12.6 g |
| Sodium sulfite | 2.0 g |
| 5-methylbenzotriazole | 3.4 g |
| 2-tert-butylhydroquinone | 0.3 g |
| 2-methylhydroquinone | 0.1 g |
| cyclopentanol | 1.0 ml |
| Carboxymethyl cellulose sodium salt | 60.0 g |
| Carbon black | 171 g |
| Distilled water to make | 1,000 ml |

The results are shown in Table 2.

TABLE 2

| Temperature | | A (Control) Dmax | A (Control) Dmin | B (This Invention) Dmax | B (This Invention) Dmin |
|---|---|---|---|---|---|
| 15° C. | Blue | 1.50 | 0.20 | 1.42 | 0.21 |
| | Green | 1.52 | 0.22 | 1.55 | 0.21 |
| | Red | 1.41 | 0.23 | 1.40 | 0.22 |
| 23° C. | Blue | 1.54 | 0.25 | 1.56 | 0.21 |
| | Green | 1.62 | 0.28 | 1.67 | 0.23 |
| | Red | 1.67 | 0.35 | 1.67 | 0.26 |
| 38° C. | Blue | 1.65 | 0.37 | 1.62 | 0.24 |
| | Green | 1.89 | 0.45 | 1.90 | 0.27 |
| | Red | 1.96 | 0.50 | 1.92 | 0.35 |

The results shown in Table 2 indicate that the film unit to which the development inhibitor releasing precursor according to the present invention, has the sufficiently low minimum density (Dmin) even when the photographic element and the processing sheet were laminated together after processing and it is understood that the effect is especially remarkable in the process at high tempepature.

EXAMPLE 5

Example 4 was repeated except that 5-{2-(m-nitrophenyl)suflonyl-ethylthio}-1-phenyltetrazole in the equivalent molar quantity was used in place of 5-(2-phenylsulfonyl-ethylthio)-1-phenyltetrazole in the processing sheet B and similar results were obtained and thus the usefulness of the development inhibitor releasing precursor of the invention was confirmed.

EXAMPLE 6

Example 4 was repeated except that 5-{2-(p-methoxy)sulfonyl-ethylthio}-1-phenyltetrazole in the equivalent quantity was used in place of 5-(2-phenylsulfonyl-ethylthio)-1-phenyltetrazole in the processing sheet B, and similar results were obtained and thus the development inhibitor releasing precursor of the invention was proved to be useful.

EXAMPLE 7

Example 4 was repeated except that 5-(2-methanesulfonyl-ethylthio)-1-phenyltetrazole in equivalent quantity was used in place of 5-(2-phenylsulfonyl-ethylthio)-1-phenyltetrazole of the processing sheet B, and similar results were obtained. Thus the usefulness of the compound as a development inhibitor releasing precursor was confirmed.

EXAMPLE 8

An intergral three color photographic element for color diffusion transfer process was prepared by coating the following layers successively in this order on an opaque polyethylene terephthalate film support of 100 μm thickness.

(1) A cyan dye-developer containing layer comprising cyan dye-developer E (11 mg/100 cm²) and gelatin (17 mg/100 cm²).

(2) A photosensitive silver halide emulsion layer comprising red-sensitive silver iodobromide emulsion (1.6 mol% of silver iodide) (14 mg/100 cm² based on silver and gelatin (12 mg/100 cm²).

(3) An interlayer comprising copolymer of butylacrylate, diaceton-acrylamide, methacrylic acid and styrene (60:30:6:4 by polymerization ratio) (18 mg/100 cm²), and polyacrylamide (0.5 mg/100 cm²).

(4) A magenta dye-developer containing layer, comprising magenta dye-developer F (8 mg/100 cm²) and gelatin (12 mg/100 cm²).

(5) A photosensitive silver halide emulsion layer comprising green-sensitive silver iodobromide emulsion (1.6 mol% of silver iodide) (10 mg/100 cm² based on silver and gelatin (10 mg/100 cm²).

(6) An interlayer comprising copolymer used in the layer (3) (10 mg/100 cm²) and polyacrylamide (1.4 mg/100 cm²).

(7) A yellow dye-developer containing layer, comprising yellow dye-developer G (8 mg/100 cm²) and gelatin (12 mg/100 cm²).

(8) A photosensitive silver ahlide emulsion layer comprising blue-sensitive silver iodo-bromide emulsion (1.6 mol% of silver iodide) (14 mg/100 cm² based on silver and gelatin (14 mg/100 cm²).

(9) A protective layer comprising 4'-methyl-phenyl hydroquinone (5.0 mg/100 cm²), N,N-diethyl lauramide (2.5 mg/100 cm²), mucochloric acid (1.0 mg/100 cm²) and gelatin (9.5 mg/100 cm²). Next, an image receiving element was prepared by coating the following layers successively in this order on transparent polyethylene terephthalate film support of 100 μm thickness.

(1) A neutralizing layer comprising half-butylester of copolymer of polyethylene and maleic anhydride (270 mg/100 cm²).

(2) A timing layer comprising copolymer of butylacrylate, diacetonacrylamide, methacrylic acid and styrene (60:30:6:4 based on weight) (55 mg/100 cm²) and polyacrylamide (1.4 mg/100 cm²).

(3) An image receiving layer comprising poly-4-vinylpyridine (11 mg/100 cm²) and polyvinylalcohol (22 mg/100 cm²).

Photographic material 5 (control) was prepared by superimposing this image receiving element onto the aforementioned photographic element.

PHOTOGRAPHIC MATERIAL 6 (THIS INVENTION)

This photographic material was prepared in the same manner as photographic material 5 except that 5-(2-benzensulfonyl-ethylthio)-1-phenyltetrazole of 0.7 mg/100 cm² each (2×10⁻⁶ mol/100 cm²) was added into the layers (1), (4) and (7) of the photographic material 5.

PHOTOGRAPHIC MATERIAL 7 (COMPARISON)

This photographic material was prepared in the same manner as photographic material 6 except that in place of 5-(2-benzensulfonyl-ethylthio)-1-phenyltetrazole 1-phenyl-5-mercaptotetrazole was used.

After each material thus prepared was given a certain amount of exposure through a silver wedge, a rupturable pod containing the following alkaline processing composition was interpositioned between each of the photographic elements and the image-receiving elements, thereby to prepare film units. Thus prepared film units were processed in the same manner as in Example 4 above. After processing each of the filn units was left alone for two hours in a room, the temparatures therein were kept at the same temperature as those of process-ing, and then reflection density of each transferred dye image was measured.

The alkaline processing composition used in this example consists of the following ingredients:

| | |
|---|---|
| pottassium hydroxide | 46 g |
| lithium hydroxide | 2 g |
| N—phenethyl-α-picolinium bromide | 10 g |
| N—benzyl-α-picolinium bromide | 20 g |
| 6-methyl urasil | 3 g |
| benzotriazole | 10 g |
| 6-benzylaminopurine | 4 g |
| polyethylene glycol (3000 in molecular weight) | 7 g |
| carboxymethyl cellulose.sodium salt | 50 g |
| titanium dioxide | 500 g |
| pH indicator dye a | 27 g |
| pH indicator dye b | 6 g |
| distilled water to make | 1000 ml |

TABLE 3

| Tempera-ture | Photographic material | Dmax B | Dmax G | Dmax R | Dmin B | Dmin G | Dmin R |
|---|---|---|---|---|---|---|---|
| 15° C. | 5 (Control) | 1.91 | 1.98 | 2.12 | 0.30 | 0.22 | 0.17 |
| | 6 (Present invention) | 1.92 | 1.97 | 2.14 | 0.29 | 0.23 | 0.17 |
| | 7 (Comparison) | 1.92 | 2.02 | 2.20 | 1.02 | 1.11 | 1.30 |
| 23° C. | 5 (Control) | 1.90 | 1.96 | 2.10 | 0.28 | 0.23 | 0.17 |
| | 6 (Present invention) | 1.93 | 2.04 | 2.13 | 0.27 | 0.22 | 0.18 |
| | 7 (Comparison) | 1.94 | 2.10 | 2.22 | 1.01 | 1.06 | 1.24 |
| 38° C. | 5 (Control) | 1.40 | 1.42 | 1.27 | 0.31 | 0.26 | 0.23 |
| | 6 (Present invention) | 1.90 | 1.92 | 1.99 | 0.30 | 0.27 | 0.24 |
| | 7 (Comparison) | 1.91 | 1.99 | 2.25 | 0.85 | 0.88 | 0.98 |

Table 3 indicates that photographic material 6 of the present invention has, in comparison with photographic materials 5 and 7, sufficiently high maximum density as well as sufficiently low minimum density at various temperatures and thus it is understood that the compound of the present invention has an excellent as a development inhibitor releasing precursor when used with a dye developer.

EXAMPLE 9

A photographic material (control) was prepared in the similar manner to that of Example 8 by coating the following layers successively in this order on an opaque polyethylene terephthalate film support of 100 μm thickness.

(1) A layer comprising red-sensitive silver iodo-bromide emulsion (Ag: 12 mg/100 cm²), cyan dye-developer H (7 mg/100 cm²) and gelatin (20 mg/100 cm²).

(2) An interlayer comprising copolymer of butylacrylate, diacetonacrylamide, methacrylic acid and styrene (60:30:6:4 by weight) (20 mg/100 cm²), and polyacrylamide (0.5 mg/100 cm²).

(3) A layer comprising green-sensitive silver iodobromide emulsion (Ag: 10 mg/100 cm²), magenta dye-developer I (8 mg/100 cm²) and gelatin (20 mg/100 cm²).

(4) An interlayer comprising the same copolymer (10 mg/100 cm²) that was used in layer (2) and polyacrylamide (1.0 mg/100 cm²).

(5) A layer comprising blue-sensitive silver iodo-bromide emulsion (Ag: 10 mg/100 cm²), yellow dye-developer J (8 mg/100 cm²), 4'-methylphenylhydroquinone (3.0 mg/100 cm²), N,N-diethyllauramide (1.5 mg/100 cm²) and gelatin (22 mg/100 cm²).

(6) A protective layer comprising tetrakis-(vinylsulfonylmethyl)methane (1.2 mg/100 cm²) and gelatin (10 mg/100 cm²).

In the same manner as the above photographic material except that 0.5 mg/100 cm² of 5-(2-benzensulfonylthylthio)-1-phenyltetrazole was incorporated into layers (1), (3) and (5) respectively, a photographic material according to the present invention was prepared.

As the support having an image receiving layer and alkaline processing composition, the same materials which were used in Example 8 were used.

Thus obtained photographic materials were exposed and processed in the same manner as in Example 8 and similar results to those from Example 8 were obtained. Thus, the photographic material according to the present invention was confirmed to have excellent photographic characteristics for wide processing temparature range.

Fluorescent brightener:

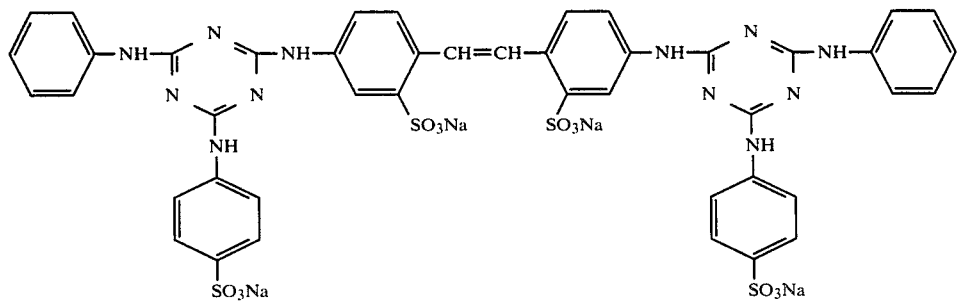

Cyan DRR compound A:

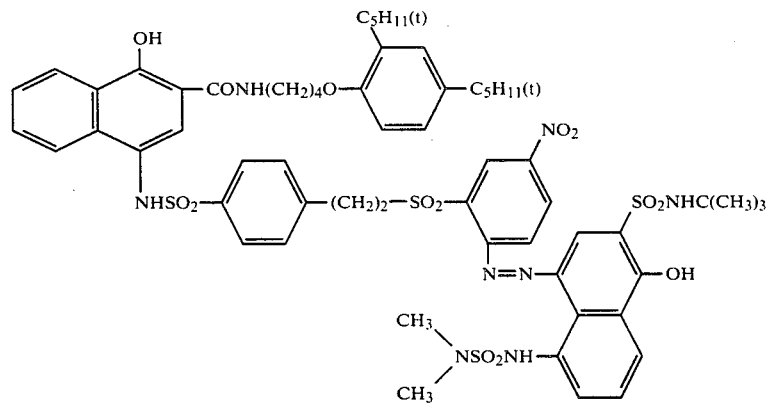

Magenta DRR compound B:

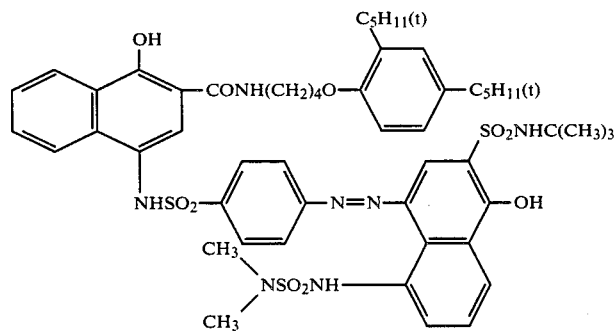

Yellow DRR compound C:

-continued
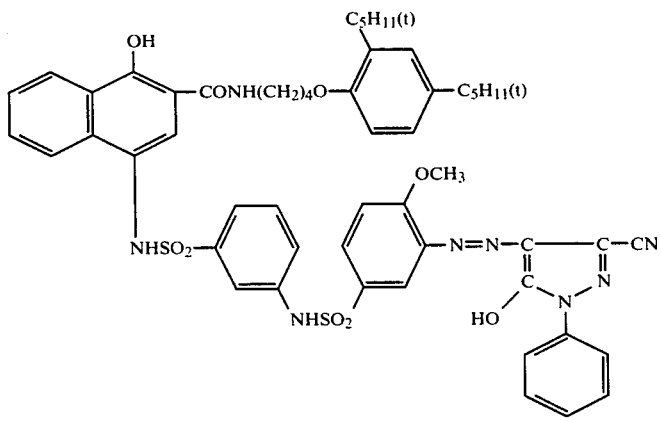
Cyan DRR compound D:
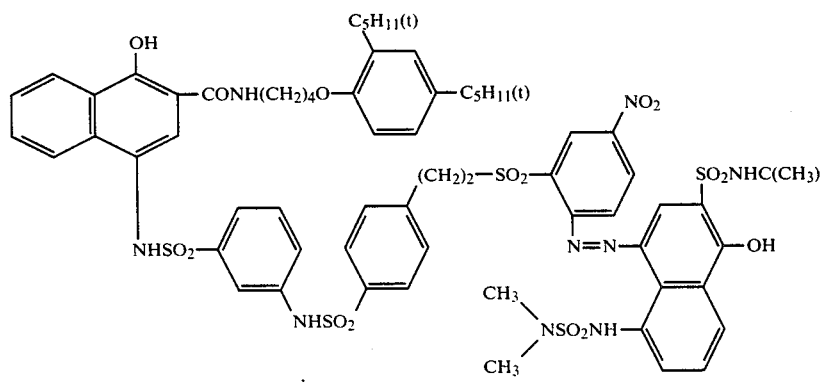
Cyan dye-developer E:
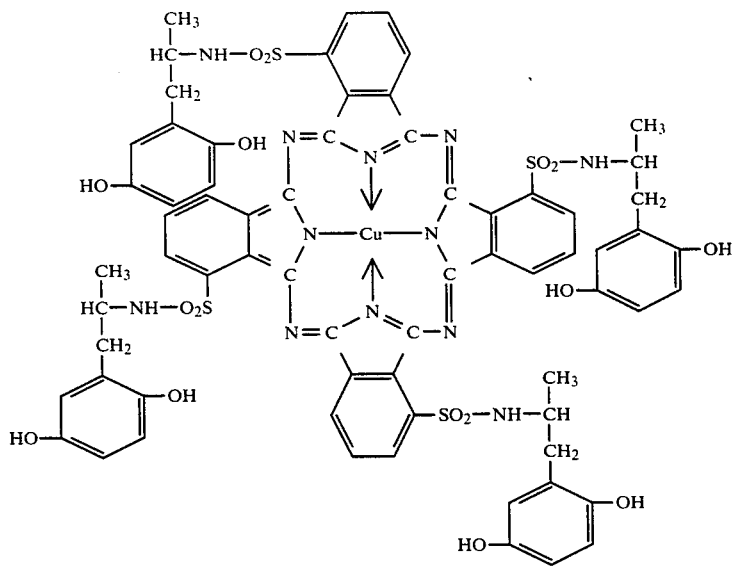
Magenta dye-developer F:

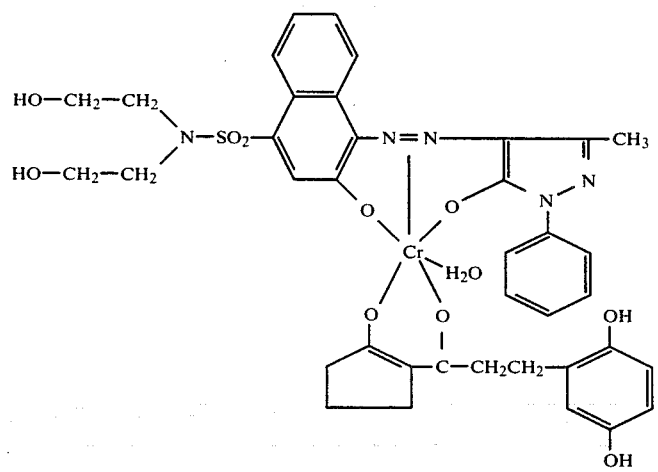
Yellow dye-developer G;
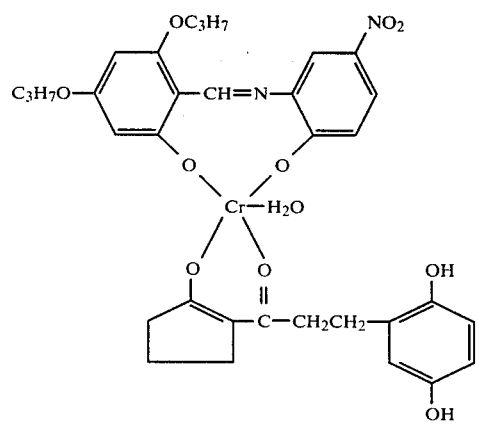
pH indicator dye a
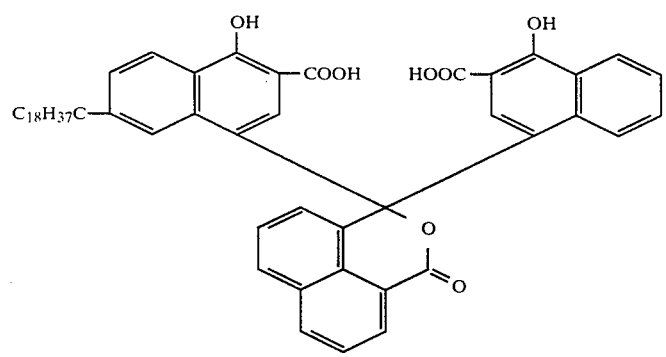
pH indicator dye b
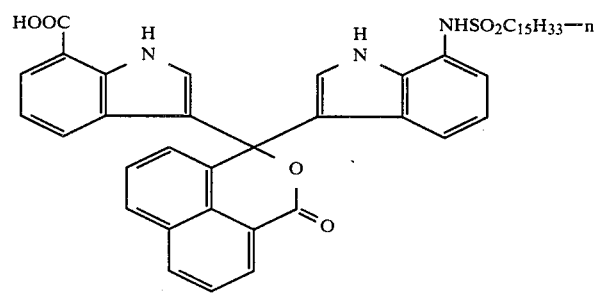

Cyan dye-developer H:

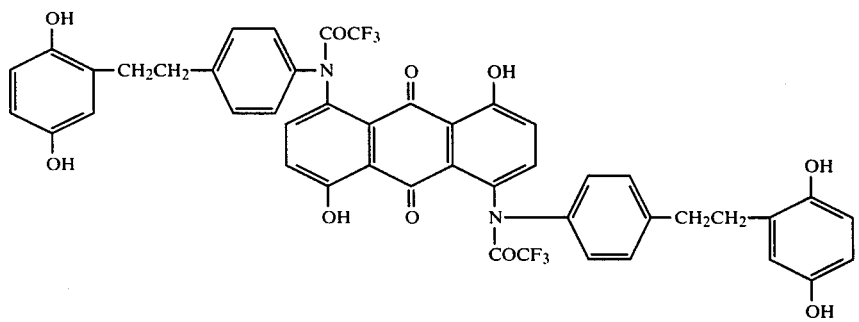

Magenta dye-developer I:

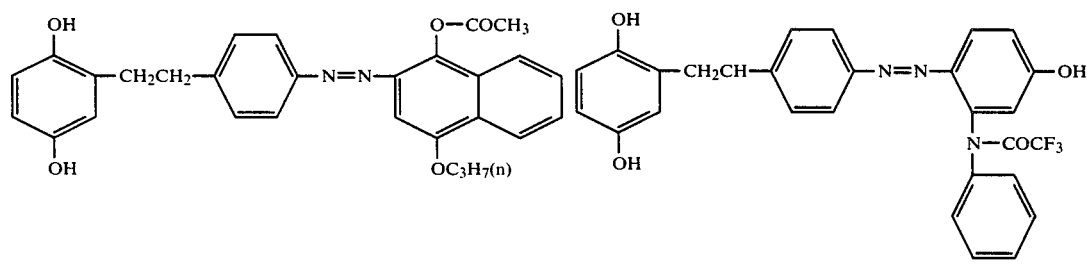

Yellow dye-developer I:

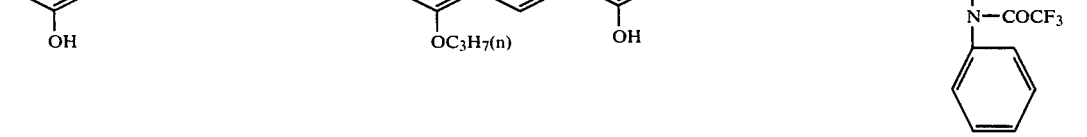

We claim:

1. A photographic material which comprises at least one photosensitive silver halide emulsion layer and a development inhibitor releasing compound represented by the following formula;

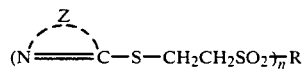

wherein Z represent non-metallic atoms necessary for forming a 5- or 6-membered heterocyclic ring, n represents an integer of 1 or 2 and R represents an alkyl, phenyl, alkylene or phenylene group provided that when n is 1, R represents an alkyl or phenyl group and when n is 2, R represents an alkylene or phenylene group.

2. A photographic material according to claim 1 wherein the heterocyclic ring is a tetrazole ring, benzotriazole ring or benzothiazole ring.

3. A photographic material according to claim 1 wherein the heterocyclic ring is a phenyl-substituted tetrazole ring.

4. A photographic material according to claim 1 wherein n is 1.

5. A photographic material according to claim 1 wherein R is an alkyl or alkylene group having 1 to 25 carbon atoms.

6. A photographic material according to claim 1 wherein R is an alkyl or alkylene group having 1 to 3 carbon atoms.

7. A photographic material according to claim 1 wherein R is an alkyl or phenyl group each of which is either unsubstituted or substituted by a electron donative group.

8. A photographic material according to claim 1 wherein the compound has a chemical structure of

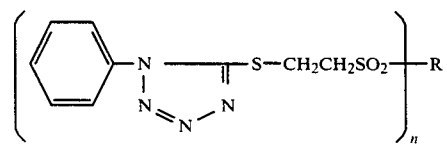

or

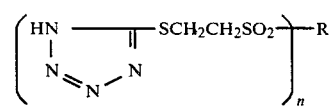

9. A photographic material according to claim 1 wherein said photographic material further comprises a dye image forming substance.

10. A photographic material according to claim 9 wherein said photographic material further comprises an image-receiving layer.

11. A photographic material according to claim 9 wherein said dye image forming substance is a dye releasing redox compound.

* * * * *